United States Patent
Spencer et al.

(10) Patent No.: US 7,604,747 B2
(45) Date of Patent: Oct. 20, 2009

(54) CHROMATOGRAPHY COLUMNS AND THEIR OPERATION

(75) Inventors: Gerald James Spencer, Abbeymead (GB); Neil John Walker, Quedgley (GB); John Mackay Scott, Chedworth (GB)

(73) Assignee: Pall Euroflow Limited, Stroud, Gloucestershire (GB)

( * ) Notice: Subject to any disclaimer, the term of this patent is extended or adjusted under 35 U.S.C. 154(b) by 118 days.

(21) Appl. No.: 10/581,968
(22) PCT Filed: Dec. 10, 2004
(86) PCT No.: PCT/GB2004/005184

§ 371 (c)(1),
(2), (4) Date: Feb. 26, 2007

(87) PCT Pub. No.: WO2005/056156

PCT Pub. Date: Jun. 23, 2005

(65) Prior Publication Data

US 2007/0138098 A1     Jun. 21, 2007

(30) Foreign Application Priority Data

Dec. 10, 2003   (GB) .................................. 0328674.7

(51) Int. Cl.
B01D 15/08 (2006.01)
(52) U.S. Cl. .................................... 210/656; 210/198.2
(58) Field of Classification Search ................. 210/656, 210/635, 659, 198.2; 95/82; 96/101
See application file for complete search history.

(56) References Cited

U.S. PATENT DOCUMENTS 4,451,365 A    5/1984  Sättler et al.
5,167,809 A  * 12/1992  Mann et al. ............... 210/198.2
5,674,455 A   10/1997  Marchand et al.
5,681,474 A   10/1997  Günther et al.
5,708,191 A    1/1998  Greenwood et al.
5,886,250 A    3/1999  Greenwood et al.

(Continued)

FOREIGN PATENT DOCUMENTS

| WO | WO 96/10451 | | 4/1996 |
| WO | WO 97/32207 | * | 9/1997 |
| WO | WO 00/00259 | | 1/2000 |
| WO | WO 00/33935 | | 6/2000 |
| WO | WO 03/076923 | | 9/2003 |

OTHER PUBLICATIONS

International Preliminary Report on Patentability (Chapter I of the Patent Cooperation Treaty) issued on Jun. 12, 2006 for the international application No. PCT/GB2004/005184.
Greenwood, M. S., et al., *Journal of Fluids Engineering*, 126(2):189-192 (2004).

*Primary Examiner*—Ernest G Therkorn
(74) *Attorney, Agent, or Firm*—Leydig, Voit & Mayer, Ltd.

(57) ABSTRACT

A method of operating chromatography column apparatus comprising a column tube (101) and first and second discrete end cell structures, associated with the respective ends of the column tube and positionable to close off the column tube and define therein a column space for retaining chromatography medium in use of the apparatus. The first end cell portion comprises a piston portion (106) fitting slidably in the column tube. The column tube and the second end cell structure are separated to provide an access spacing between them. The piston portion (106) of the first end cell structure is advanced through the column tube to expose it at the open second end of the column tube, for maintenance of the piston portion thus exposed. Corresponding chromatography apparatus is another aspect of the disclosure.

12 Claims, 10 Drawing Sheets

U.S. PATENT DOCUMENTS

| | | |
|---|---|---|
| 6,082,180 A | 7/2000 | Greenwood |
| 6,082,181 A | 7/2000 | Greenwood |
| 6,117,317 A | 9/2000 | Dickson et al. |
| 6,190,560 B1 | 2/2001 | Mann |
| 6,558,539 B1 | 5/2003 | Mann |
| 6,736,974 B1 | 5/2004 | Mann |
| 6,763,698 B2 | 7/2004 | Greenwood |
| 6,877,375 B2 | 4/2005 | Greenwood |
| 2004/0099604 A1* | 5/2004 | Hauck et al. ............ 210/656 |
| 2006/0124525 A1* | 6/2006 | Bellafiore ............ 210/198.2 |

* cited by examiner

SECTION A-A

SECTION C-C

SECTION B-B

SECTION D-D

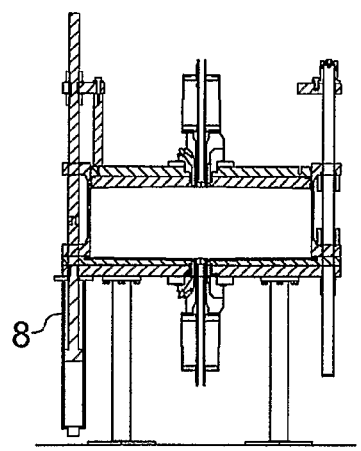
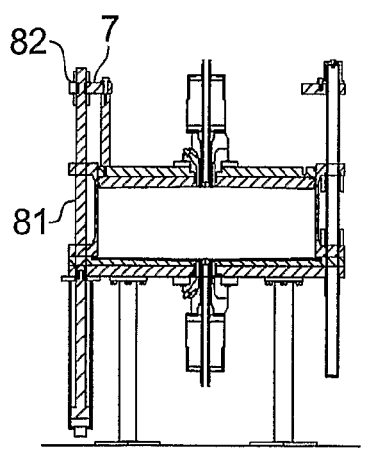
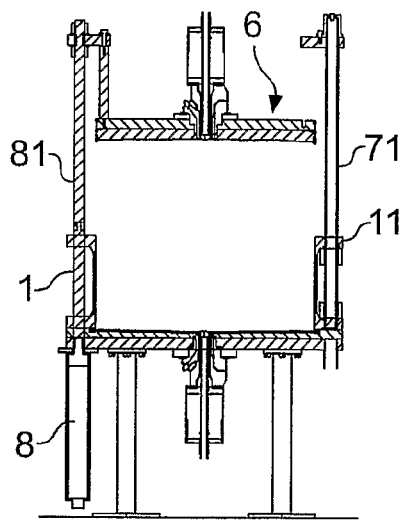
SECTION E-E
Fig. 3a
SECTION G-G
Fig. 4a
SECTION I-I
Fig. 5a
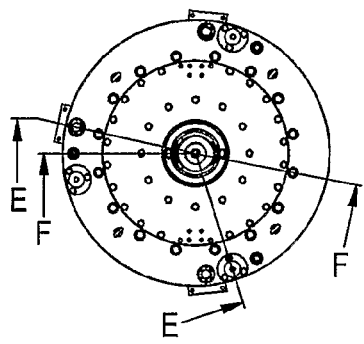
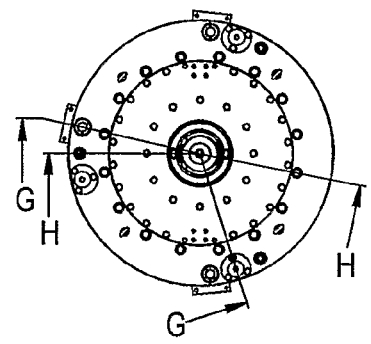
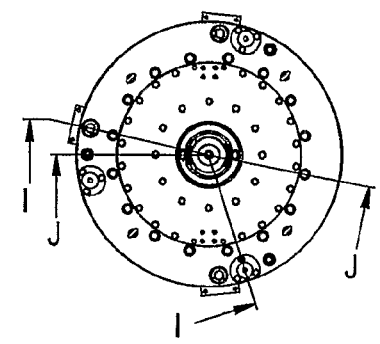
Fig. 3b
Fig. 4b
Fig. 5b
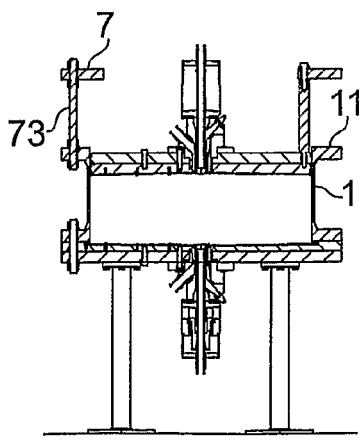
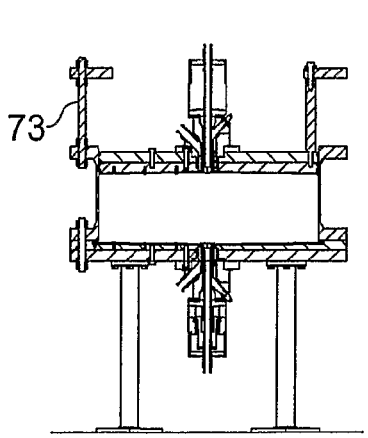
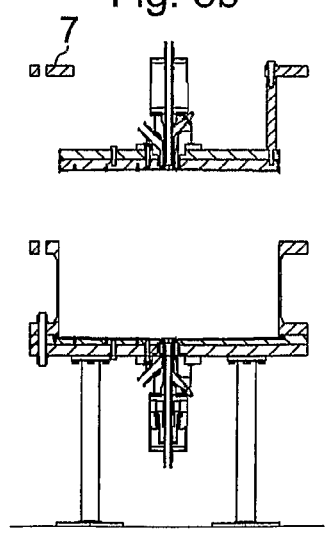
SECTION F-F
Fig. 3c
SECTION H-H
Fig. 4c
SECTION J-J
Fig. 5c

SECTION A-A

SECTION A-A

SECTION B-B

SECTION B-B

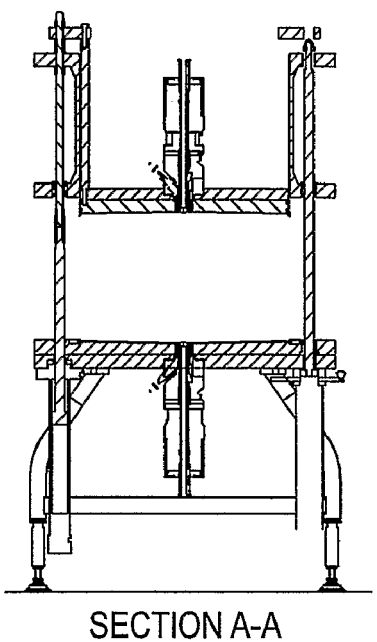
Fig. 12a
SECTION A-A
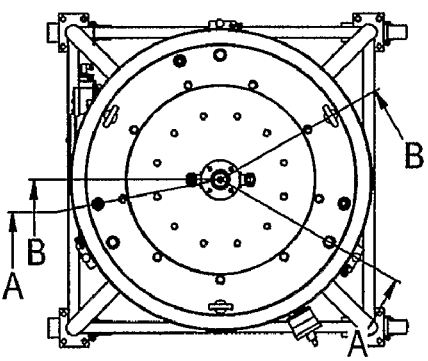
Fig. 12b
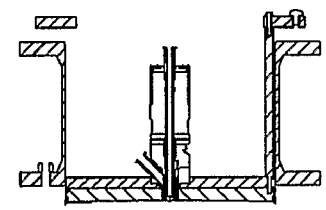
Fig. 12c
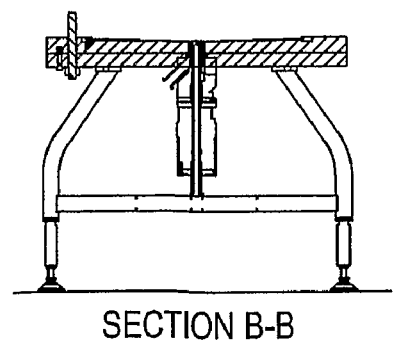
SECTION B-B

CHROMATOGRAPHY COLUMNS AND THEIR OPERATION

REFERENCE TO RELATED APPLICATIONS

This application is a 371 of PCT/GB04/05184 filed Dec. 10, 2004

FIELD OF THE INVENTION

This invention has to do with chromatography apparatus and methods. It is particularly concerned with systems and methods for gaining access to components of the column e.g. for maintenance, notably the column end cell structures.

BACKGROUND OF THE INVENTION

The present discussion relates to apparatus and methods useful in industrial-scale chromatography, e.g. large-scale preparative purification of fine chemicals and pharmaceuticals, including biological products. It is not concerned with laboratory-scale apparatus. Conventionally an industrial-scale chromatography column has a cylindrical axially-vertical column tube with top and bottom end cells, each of which provides a strong backing plate with a fluid inlet/outlet and support for a layer of mesh, sinter or other fluid-permeable retaining material which lets process liquid flow into and out of the chromatography space while retaining the bed of particulate chromatography medium. To provide adjustability and control of bed height and bed compression, at least the top end cell is usually made in the form of a piston slidable in the column tube interior. The bottom end cell may also be a piston but more usually is a fixed plate bolted against a bottom end flange of the column tube. Typically this bottom plate acts as a support for the column as a whole, being itself supported on legs or some other stand arrangement leaving clearance for outlet pipework projecting beneath the bottom end cell.

Various mechanisms are known for controlling the position of the piston end cell. The structure supporting the piston must move into the column interior behind the piston, and so must be smaller than the column diameter. Usually metal spacer posts are fixed to the back of the end plate and extend up axially—to a distance corresponding roughly to the length of adjustment anticipated—to a lifting ring which is connected in turn down to an external drive and support mechanism able to move the end cell piston, via the spacer posts, relative to the fixed mounting. For example a set of lifting rods may extend up axially outside the column from the fixed mounting to the lifting ring. The lifting rods include (or are connected to) an axial drive, usually a mechanical threaded drive which may be hand-operated, to move the lifting ring up and down and thereby control the position of the end cell piston in the column. Because the piston is large, close-fitting and acts on a bed of fluid or particulate medium which may be packed, it is crucial that the rate of raising or lowering the piston be carefully equalised around the column and this requires care and time.

In the prior art, U.S. Pat. No. 5,681,474 describes a chromatography column in which the top end cell plunger is carried by three rods connected to hydraulic drive cylinders, operated from a central control to preserve alignment of the top cell as it is forced down onto the media bed, especially to achieve flow packing.

WO 00/00259 describes a column in which the top end cell can be fully retracted from the column tube by means of a set of threaded rods driven in rotation.

Columns marketed by Chromaflow in the mid 90's also featured hydraulic drives to move and if necessary withdraw upper and lower end cell plungers relative to the column tube.

From time to time in certain kinds of columns and processes it may be desirable or necessary to get access to the column interior for purposes other than filling or emptying particulate medium, especially since columns are now available which can do the latter through valved ports. In particular, column maintenance may require access to the inner parts of the end cells e.g. to remove their permeable retaining layers (mesh or sinter) and/or their seals, for cleaning, replacement or repair. For such access, the end cell must be withdrawn and separated from the column tube, either entirely or at least with enough clearance to carry out the operation in question, e.g. removal/insertion of a permeable layer element or seal. Typically access to the lower permeable element is by unbolting a lower column tube flange from the bottom end cell plate, and lifting the column tube up away from the plate sufficiently to unfasten and remove the permeable element sideways. Access to the permeable element of the top (piston) end cell is by lifting the piston right out of the column tube using the mechanism provided, sufficiently far for the permeable element to be moved in or out sideways.

The column elements being heavy, these operations normally have to be done with the aid of cranes, powered drives or by manual mechanisms with substantial mechanical advantage. For the same reason, alignment structures are used to keep the column and its end cells axially aligned as they are separated from each other as described. This avoids potential serious damage to precision components. The alignment and lifting structures cause significant obstructions around the tube, and need to be carefully laid out to provide sufficient clearance at some part of the circumference for insertion/removal of the permeable retaining elements if this is to be an operational requirement.

By way of illustration, a system and method working in line with known principles (see U.S. Pat. No. 6,736,974) are described with reference to FIGS. 1 to 5, in which FIGS. 1 and 2 show first and second stages for access to a lower end cell mesh, and FIGS. 3, 4 and 5 show first, second and third stages for gaining access to the upper end cell mesh. In each Figure, views (a) and (c) are axial sections at the lines indicated in the top view (b).

First, the basic elements of the apparatus are described with reference to FIGS. 1 and 2. A chromatography column consists essentially of a steel column tube 1 mounted on a bottom base plate 5, supported on the ground through a set of legs 51. The column tube has integral top and bottom flanges 11,12 projecting perpendicularly around its top and bottom edges. The base plate 5 consists of a lower support plate 52 with a flat upper surface and an inner contoured cell plate 53. The cell plate 53 has a contoured surface with an array of support projections and intervening conduits (not shown) on which a permeable element (lower end mesh) lies and is held in place by an array of fasteners. A multiport access valve 55 communicates with the space above the cell plate through a central orifice in the bottom plate 5 to enable unpacking of chromatography medium and collection of eluent in processing; this is all established technology. The bottom tube flange 12 seats down around the edge of the base plate 5, compressing peripheral seals and clamping the edge of the mesh, and is secured there by bolt or stud fasteners 57.

The top cell 6 likewise has a rigid flat backing plate 62 and an inner contoured cell plate 63 for supporting an end mesh (not shown), but unlike the bottom end cell is configured as a piston slidable inside the column tube. It is supported from above through a circumferentially-distributed array of vertical (axial) spacer rods 66 whose bottom ends are screwed rigidly into the cell's backing plate 62, while their top ends screwed up into the inner periphery of an annular adjuster flange 7. The adjuster flange 7, sometimes called a lifting ring, is spaced coaxially above the top column tube flange 11 and has the same OD but a smaller ID, so that it overhangs the column interior for securement to the spacer rods 66 that hold the piston 6.

Fluid communication through the top end cell 6 is through another central access valve 65, similar to that in the bottom plate 5. Among other functions, these access valves enable particulate medium to be packed into and unpacked from the bed space of the column as a slurry, without opening the column.

Three vertical guide rods 71 have their top ends fixedly threaded into the adjuster flange 7 at spaced locations (see views (b)). Each of these guide rods 71 descends with clearance through a set of aligned guide holes through the upper and lower column tube flanges 11,12 and the periphery of the column base 5.

Hydraulic drive cylinders 8 are mounted vertically on the underside of the outer base plate 52, and their driven rods 81 extend up through further sets of aligned holes in the base 5, upper and lower column tube flanges 11,12 and adjuster flange 7. Each lifting rod 81 is threaded near its top and has a pair of locating nuts 82 to either side of the adjuster flange 7 for fixing the flange to the rod 81 at a selected position. In this example there are three drive cylinders 8.

Further connecting structure is provided by a set of three vertical tie bars 73. These are short threaded rods received in openings through the adjuster flange 7 and top column tube flange 11, with respective pairs of locking nuts 74,75 to fix the location of each of these engagements.

Operation of the drive cylinders 8 directly raises or lowers the adjuster flange 7, to a height determined by the location of the drive rod locknuts 82. The top end cell piston 6, being rigidly connected to the adjuster flange 7 through the spacer rods 66, is raised or lowered correspondingly. If the tie rods 73 are locked by their locating nuts 74,75 to both the adjuster flange 7 and column tube flange 11, the drive rods 81 will lift the column tube 1 as well provided that it has first been released from the base 5 by releasing the studs 57.

The following description of maintenance steps can now be followed.

To remove or gain access to the lower mesh or seals, the hydraulic cylinders are fully retracted to set the piston 6 to its lowermost position. The studs 57 holding the column tube 1 to the base 5 are removed. The tie rods 73 are locked to the upper column tube flange 11. Refer to FIG. 2. The hydraulic cylinders are then extended raising the adjuster flange 7, column tube 1 and top cell 6 away from the base. The guide rods 71 slide through their aligned holes in the base to keep the components in line and protect the hydraulic lifts from lateral forces. In this condition the lower mesh can be detached from its mounting 53 and removed through the clearance between column tube 1 and base 5. Note in views (b) that the guide rods 71 are circumferentially spaced more widely to the right of the view, providing a larger opening there for passage of the mesh assembly.

Next, the known mode of removal of the upper mesh is described with reference to FIGS. 3, 4 and 5. Essentially the top piston 6 has to be lifted out above the column tube 1. To achieve this, the piston 6 is raised by the drives 8 to maximum operating height in the column, the tie rods 73 then being at full reach (FIG. 3). The tie rods are then locked at the adjuster flange 7 and tube flange 11, so that the adjuster flange 7 is supported fixedly by the column tube 1 and tie rods 73. The drive rods 81 can then be released from the flange 7, fully retracted and re-fastened with a new location on the flange 7 giving extra reach: see FIG. 4. The tie rods 73 are then fully released, and full advance of the hydraulic drives lifts the piston end cell 6 clear above the column tube 1 as seen in FIG. 5. The upper mesh can then be removed through the resulting clearance, between the two right-hand guide rods 71 which as before maintain the alignment of the components, and which by locking relative to the base 5 and or tube 1 support the piston 6 in its raised position. Throughout this operation the tube 1 preferably remains bolted to the base 5.

The described procedure and apparatus provide access to the two end cells without requiring overhead lifting equipment. Industrial columns can be very large and heavy; typically the column diameter is 500 mm or more. The illustrated column has a 1400 mm diameter and would be very difficult to manoeuvre without a powered lift.

The described apparatus and procedure have however the drawback that access to the upper mesh is difficult; it has to be removed at quite a distance above the ground. For such a large and delicate component this is a significant issue.

We also note the system described in WO 03/076923, which gets access to the top end cell piston by connecting the piston centrally to an overhead yoke. Once the piston has been lifted to the top of the column tube, this yoke can be released at one side and swung up and over to bring the piston (inverted) down beside the column. This gives lower access in the final position, but the swinging over of the piston would be a risky matter with a large column, so that this proposal is limited to smaller columns.

SUMMARY OF THE INVENTION

Aspects of our new proposals are new apparatus and techniques for improving access to the piston end cell in operations of this kind.

A first aspect of our proposals is a method of operating chromatography apparatus, the apparatus comprising a column tube having first and second ends, and first and second discrete end structures associated with the respective ends and defining with the column tube a column space for retaining chromatography medium in use of the apparatus, at least the first end structure comprising a piston portion fitting slidably in the column tube. In the method, the column tube is separated from the first and second end structures to provide access to those structures, e.g. for inspection, cleaning, repair, replacement or exchange or the like of parts, such as seal(s) and permeable retaining members (conveniently referred to herein using "maintenance" as a collective term). The characteristic feature in our first proposal is that access to the first end structure is provided by moving the piston thereof forwardly through the column tube to expose it at the open second end of the column tube, which is separated from the second end structure to give access.

Compared with existing methods, this has the radical advantage that the access positions for the first and second end structures can be relatively close to one another. In the preferred orientation, where the first end and second end are the top and bottom respectively, the first end structure appears below the column, greatly reducing the potential access height requirement. Separation of the second end structure from the column—necessary for access to the second end structure—is also involved in access to the first end structure, potentially simplifying the procedure e.g. compared with that described above with reference to FIGS. 1 to 5 in which the column tube had to be lowered onto the base to expose the top piston, inevitably covering the bottom end cell. In the present procedure, both may be accessible at the same stage.

The second end structure (usually the bottom) may remain fixed. The column tube may then be released from the fixed second end structure and moved away from it axially to a position spaced from it. Then the piston of the second end structure is moved through the column towards the second end structure and emerges at the second column end, the tube and second end structure remaining fixed during this movement. This is most obviously practical where the first end is at the top and the column is an upright column on a stand. However different types of movement may be appropriate, e.g. to hold the column tube and lower the second end structure away from it.

Preferably a powered drive such as a hydraulic drive is used to space the column tube from the second end structure, and move the first end structure's piston through the column tube to its exposed position. Preferably the same drive performs both functions. Preferably the drive is mounted on or adjacent the second end structure.

For the piston to be moved right through the column, it needs to be supported from behind by a structure that can fit into the column tube behind it, essentially over the full length of the tube. This insertable piston support structure desirably connects the piston to an operating drive, preferably a powered drive such as a hydraulic drive, throughout its stroke including the position exposed at—and preferably projecting from—the second end, so that it can be driven controllably to and from the exposed position.

We talk here about pushing the piston through the tube; it should be understood that except where the context specifies otherwise this is a relative matter and may involve absolute movement of the tube while the piston remains fixed, or movements of both elements over different distances. The preferred combination of movements will depend to some extent on the dimensions of the components, the operating stroke available for the drive(s) used, and on whether (as preferred) the same drive(s) is/are used for the operations exposing the end structures as is/are used for adjusting the position of the mentioned piston when the column is closed for operation.

In apparatus terms, chromatography apparatus embodying the invention has a column tube, first and second end structures as described above, and means for driving relative movement between the column tube and end structures from a closed position, in which the first end structure's piston is fitted inside the tube and the second end structure closes the second end of the tube, and an open (maintenance) position in which the second end of the column tube is held spaced away from the second end structure, and the piston of the first end structure is exposed at the second end of the tube and preferably projecting beyond it. Preferably the drive arrangement supports the piston axially via a drive support behind the piston, i.e. having an insertion structure which extends along inside the column tube in the maintenance position. The drive means which carries out this function may drive the column tube and/or the piston relative to the second end structure; the drive source is preferably fixed on or fixed relative to the second end structure, and preferably adjacent that structure. Preferably the drive means is fixed directly to the second end structure, e.g. a base of the column. To drive the piston, the drive means may have a piston drive connector extending axially outside the column from the second end to the first end, and connecting past the first end with an insertable support structure for the piston as mentioned above. Preferably the drive is via axially-movable rods extending up beside the column, e.g. hydraulically-driven rods. A radial connecting structure, such as a lifting ring or adjuster flange as referred to previously, may form a part of the drive connector which connects these rods to the insertable piston support structure. The insertable structure itself may be a set of axial rods extending back from the piston, as in previous constructions, but of a length enabling the piston to emerge at the second end of the column tube.

Preferably a common drive operates both the relative movement between a piston and second end structure and the relative movement between the column tube and first end structure. For this purpose, somewhat analogous to the structure described previously in relation to FIGS. 1 to 5, the drive connection may be selectively connectable/disconnectable to the column tube and/or second end structure, so that they can be moved either together or relative to one another. However there is no need for connections dedicated to union of the column tube and second end structure (cf. the tie rods 73 referred to previously) because this mode of movement may not be needed.

By operating the drive from one end, in practice preferably the base of the column which may be a base mounted on a stand, we can provide the advantages of the invention without relying on overhead structures or separate units. Nevertheless, the skilled person will appreciate that the advantageous exposure of the piston at the opposite end of the column tube may be achieved by other means if extra drives or attachments to other structures are tolerated, e.g. to drive the piston down from a fixed structure above, and/or to lift the column tube up or down relative to its base e.g. by a similar means, or to support the tube and drive the base downwardly. In general, use of dedicated drives for the different functions simplifies the drive connections but makes the apparatus more bulky, complicated and expensive overall, to the extent that it may be difficult to mount the various drives while retaining adequate access to the column area.

As in previous proposals, it is preferred to have one or more non-driving guide structures engaging the relatively axially moveable column components to maintain and support their axial alignment as they are driven in relative movement. For example, plural slidable guide rods passing through openings in the components may be used as described previously. Mechanisms are preferably provided for locking relative to these structures e.g. guide rods in selected positions, so that components can be held at selected spaced orientations (particularly for access) without relying on (or relying solely on) the drive for this purpose. A skilled person will appreciate that there are other ways of providing detents for holding various axial positions of the components, for safety or otherwise.

Safety stops may also be provided for limiting the extent of available axial movement between various components to prevent their exceeding the safe reach of the structure; these also may be embodied in rods or tensile elements with stop abutments engaging between the components in question. The guide rods can be used for this. In present embodiments, the guide rods need not connect to the lifting ring.

Typically these proposals are useful with columns whose column tubes are at least 500 mm in internal diameter, or preferably 800 mm or more, or 1000 mm or more. The height of the column tube is preferably at least 200 mm, more preferably at least 300 or at least 400 mm. It may be used with integrally flanged steel columns or with polymer tubes held between discrete flange plates.

Because the usual use of the system is for gaining access to the permeable elements of the first and second end structures, the disposition of axially-extending surround and drive structures needs to be determined in conjunction with the axial clearances achieved by the mechanism so that there is room to get these permeable elements in and out.

Preferably the invention is implemented in a column having one or more packing and/or unpacking valves enabling the column to be filled with or emptied of packing medium as a slurry. These may be combined valves also providing for flow of process liquids, and preferably access the column interior through the centre of each end structure, bypassing the permeable structure.

While the particular kind of drive used for moving the tube and end structures axially relative to one another is not particularly limited, and indeed these movements may be done manually if necessary, it is preferred to use a hydraulic drive with plural hydraulic drive units distributed around the column. The skilled person is well aware that where a piston end cell is moved in a column tube, it is important to preserve exactly the axial alignment of the piston in the tube. This is not straightforward where it is wide, heavy, subject to large forces and supported at more than one point. In this respect, we propose to detect the axial positions of plural circumferential drive components (acting on the piston), input the detected positions to a control processor, and use the control processor to compare the detected positions with one another and/or with a predetermined value. The control processor is programmed then to control and adjust the rates and/or pressures of supply of hydraulic fluid to the respective hydraulic drive units to keep the piston axially aligned as it moves. This proposal is new and useful in any chromatography column using multiple hydraulic drives for the end cell piston; it is itself a separate aspect of our proposals and not limited to the particular mechanisms described above as aspects of the invention.

Returning however to the maintenance proposals, it is preferred that in the maintenance position the first end structure's piston actually projects from the column tube's second end, and more preferably sufficiently far to expose a peripheral outwardly-directed seal of the piston. When retracting the piston towards the operational condition, this seal structure rides over the edge of the column tube and might be liable to damage. It may therefore be desirable to adapt the seal structure and/or column tube conformation at this point to avoid such damage. The top opening of a column tube conventionally has a guide chamfer for this purpose, but this is usually undesirable at the bottom end because uniformity at this region is critical for chromatography. Therefore it is preferred to adapt the seal structure, such as by providing a projecting annular support e.g. of engineering plastics, closely axially adjacent a sealing ring to protect it against possibly damaging deformations as it retracts into the tube.

BRIEF DESCRIPTION OF THE SEVERAL VIEWS OF THE DRAWINGS

A system and method working in line with known principles (see U.S. Pat. No. 6,736,974) are described with reference to FIGS. 1 to 5, in which FIGS. 3, 4 and 5 show first, second and third stages for gaining access to the upper end cell mesh. In each Figure, views (a) and (c) are axial sections at the lines indicated in the top view (b).

Figure 1A:
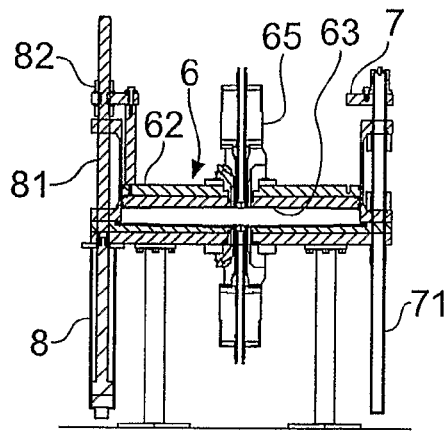
FIGS. 1 and 2 show first and second stages for access to a lower end cell mesh.
Figure 2A:
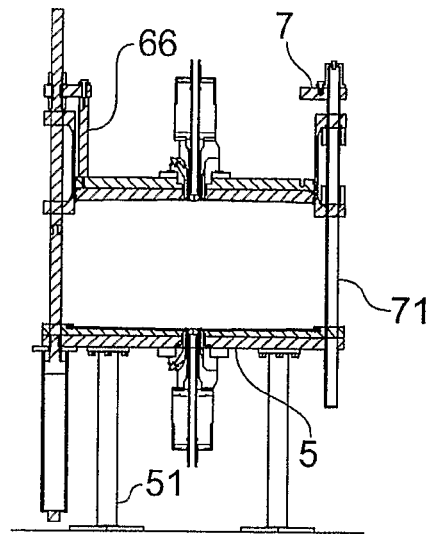
Figure 1B:
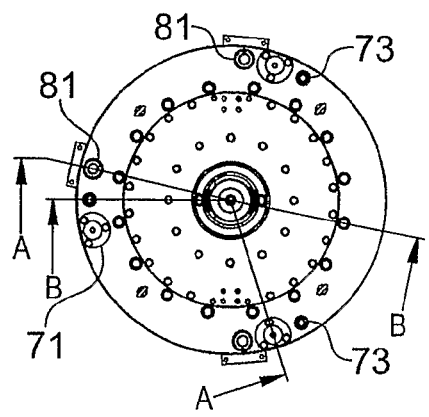
Figure 2B:
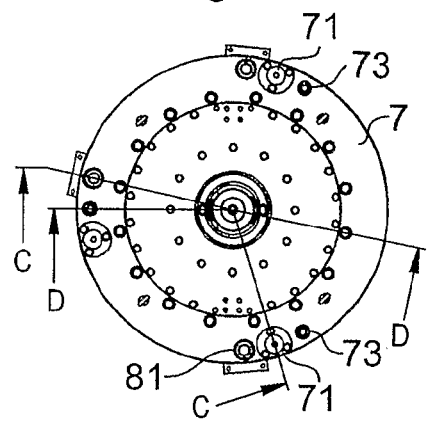
Figure 1C:
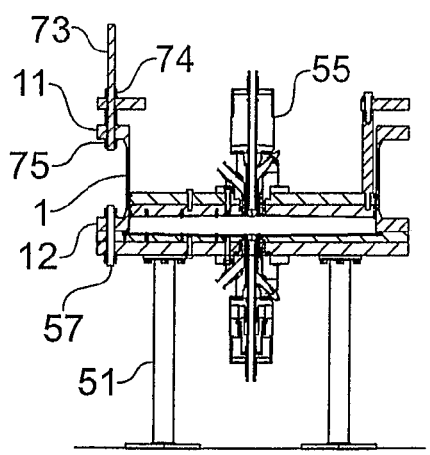
Figure 2C:
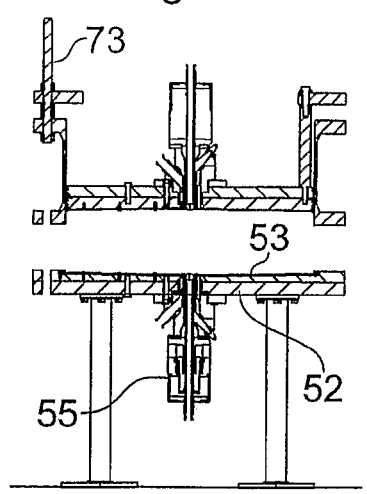
Figure 6:
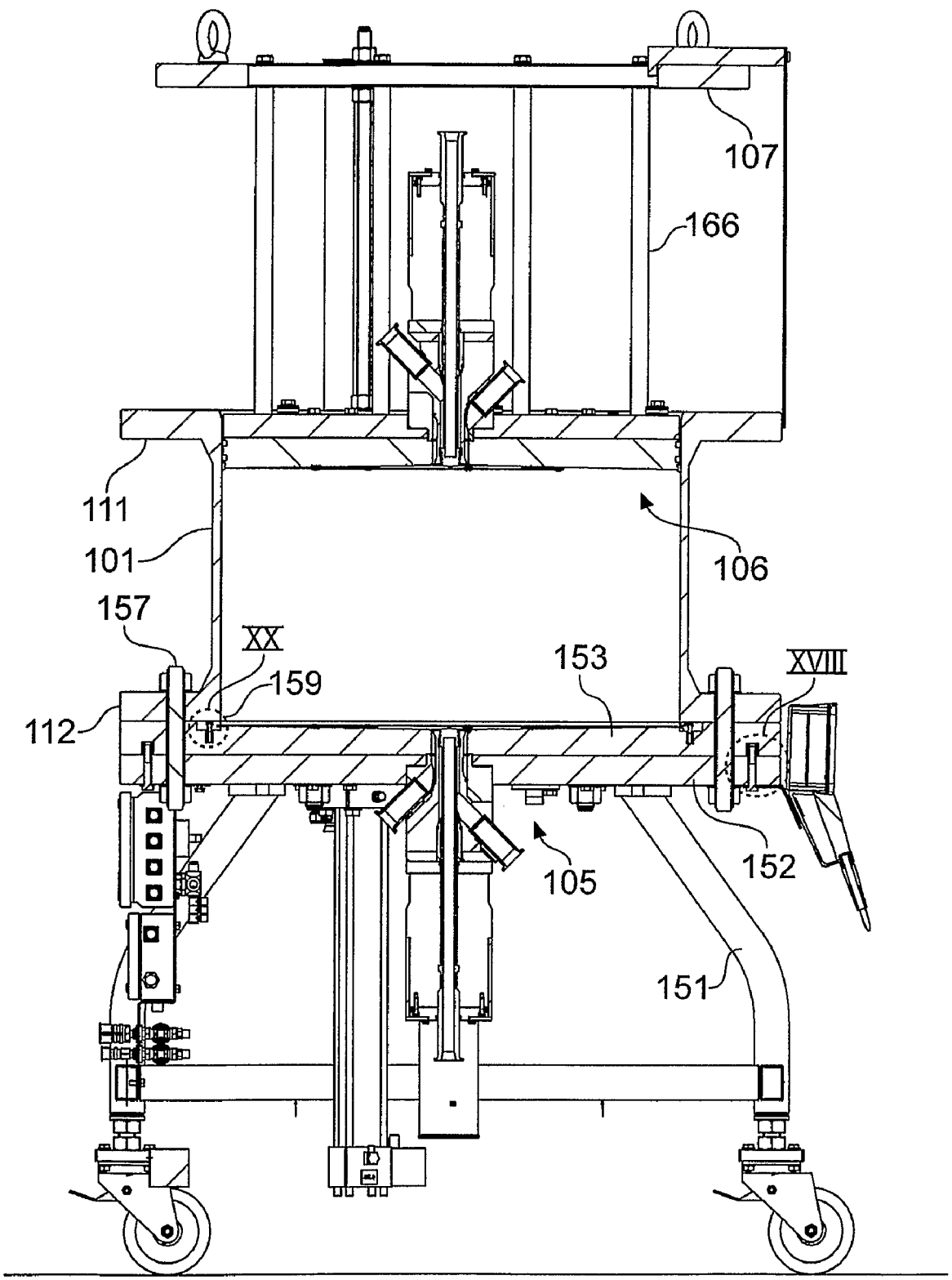
Figure 7:
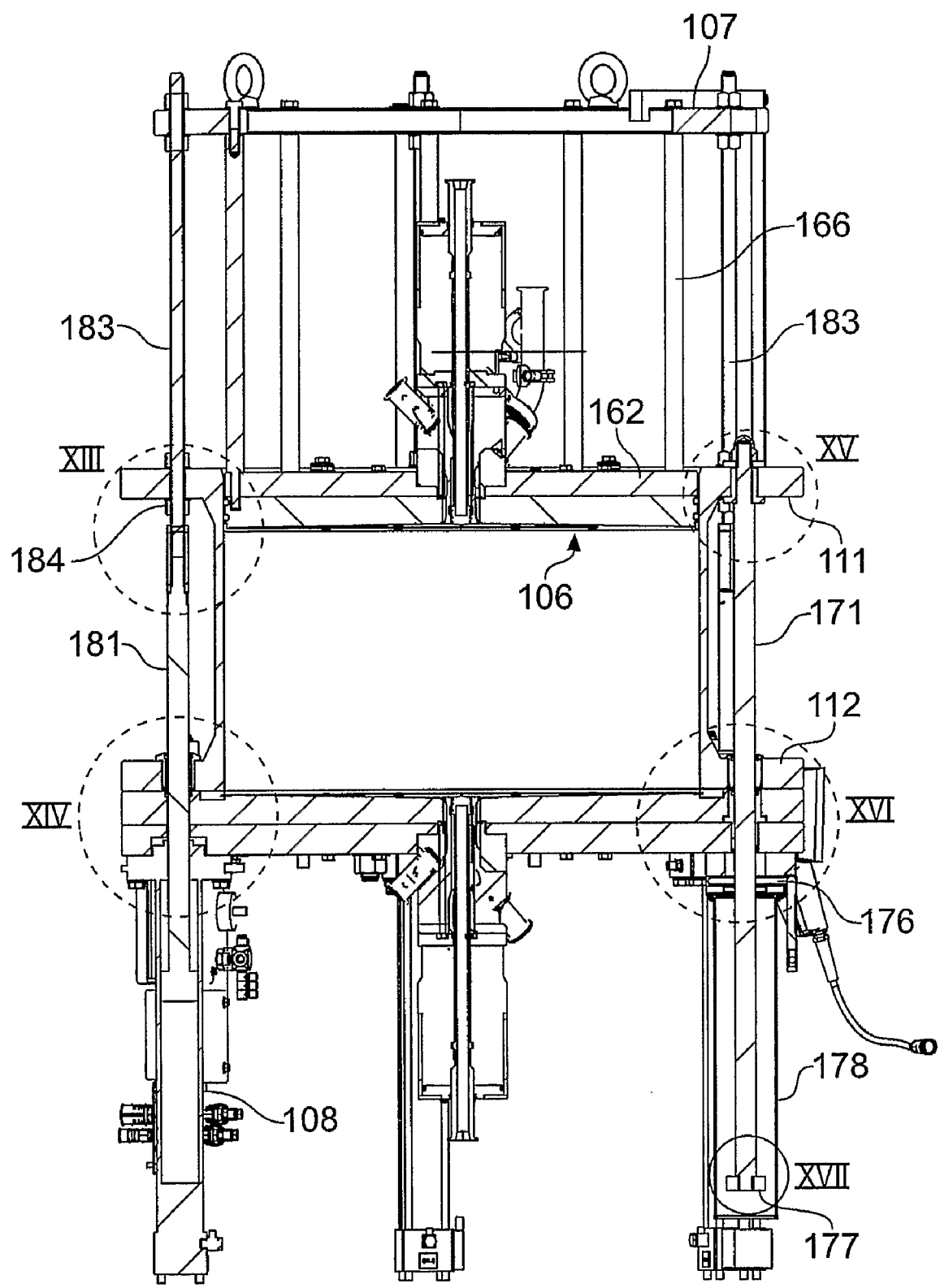
Figure 9:
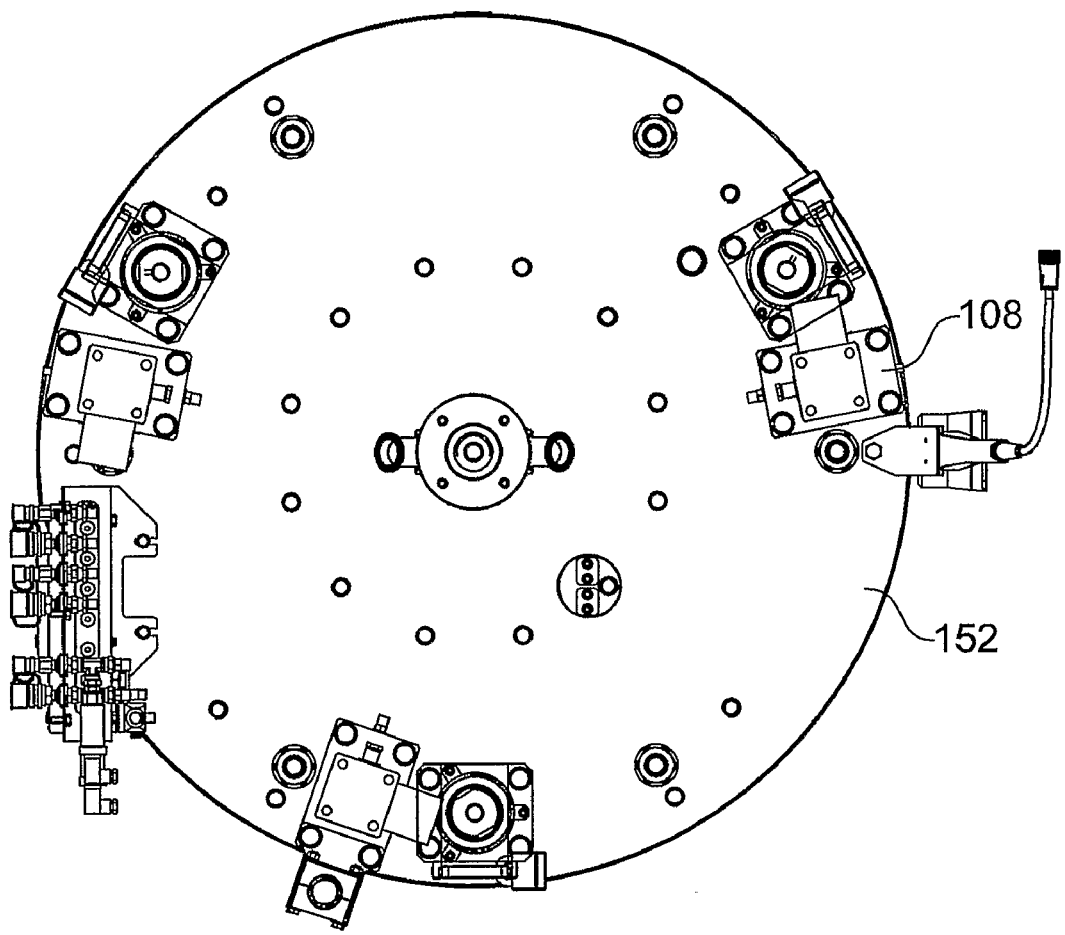
Figure 8:
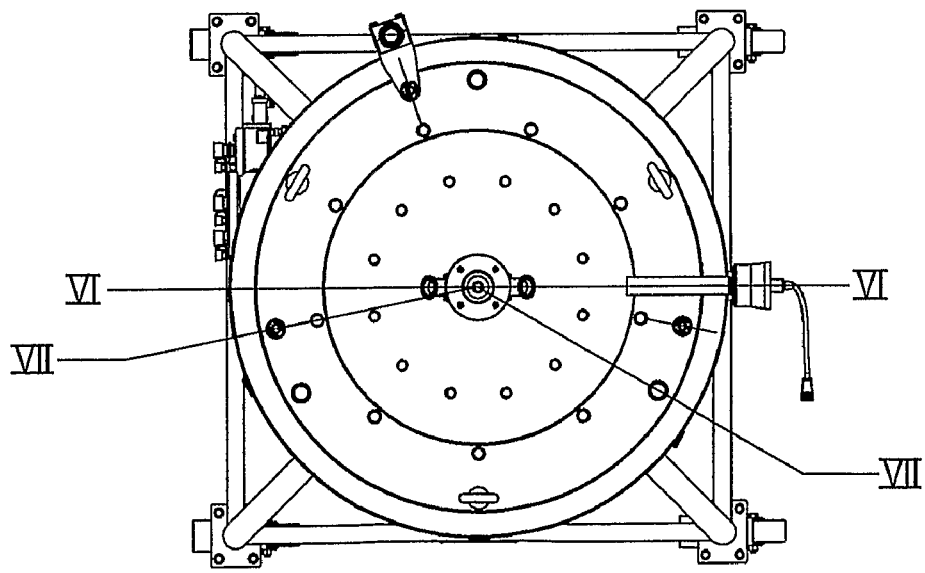
Figure 10A:
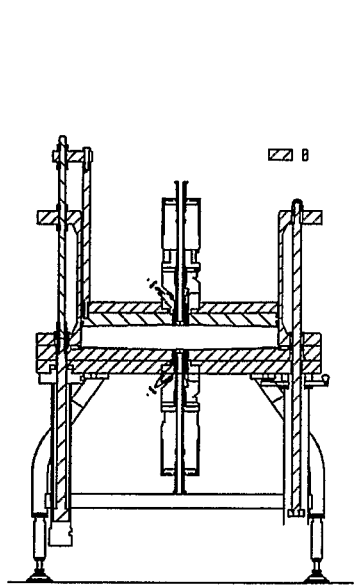
Figure 11A:
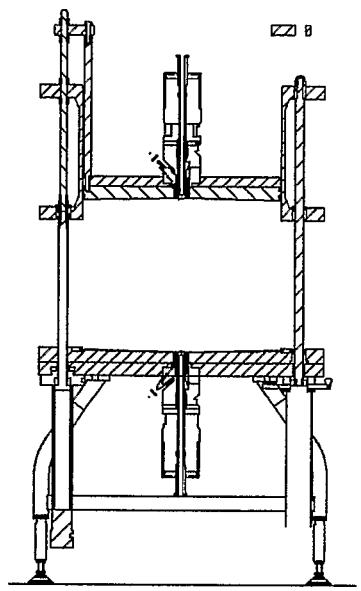
Figure 10B:
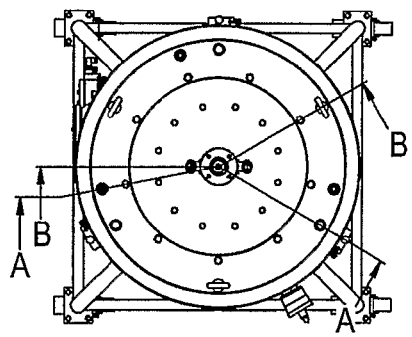
Figure 11B:
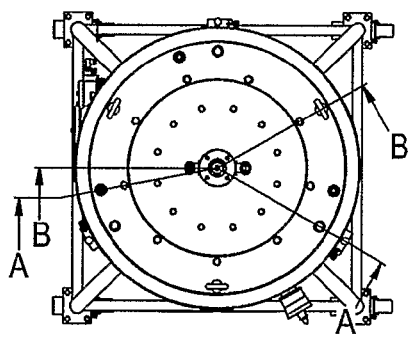
Figure 10C:
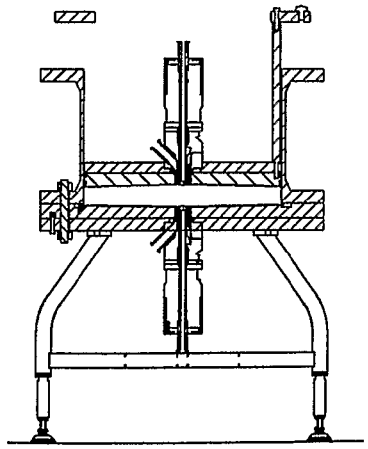
Figure 11C:
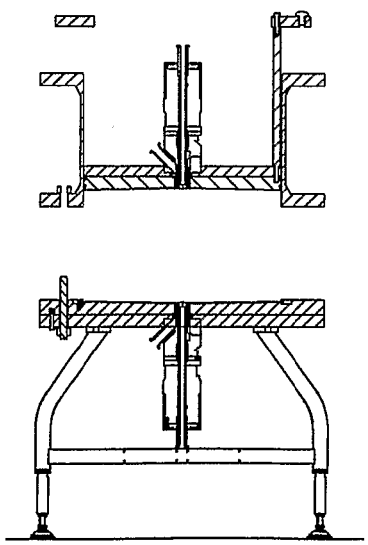
Figure 13:
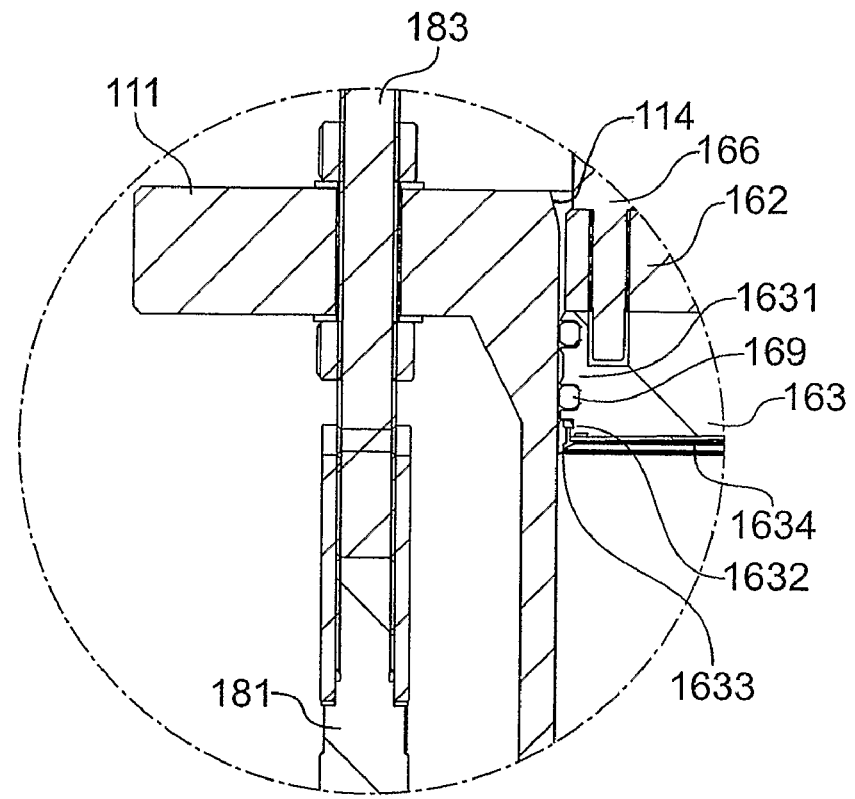
Figure 14:
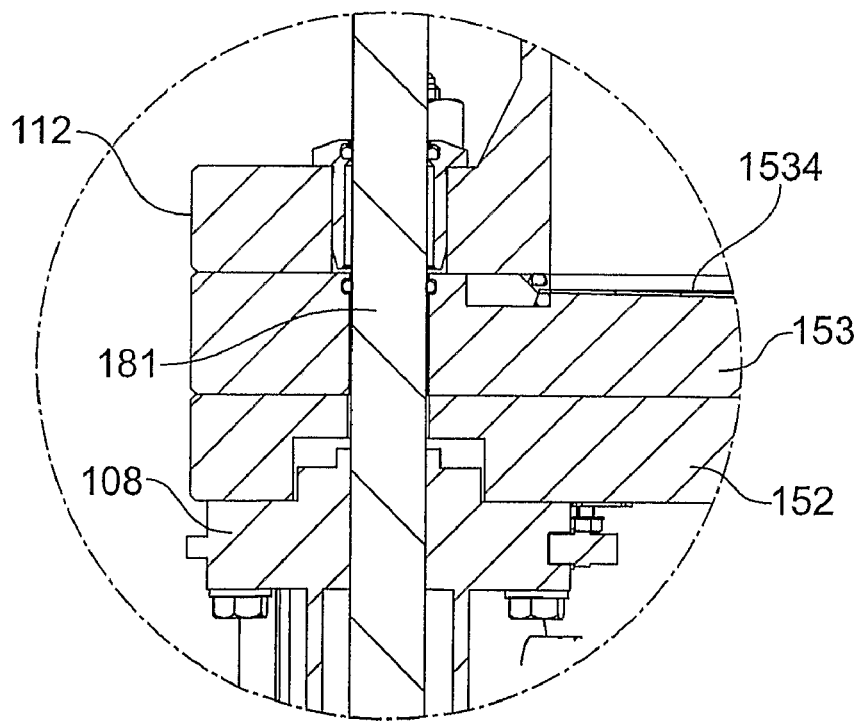
Figure 15:
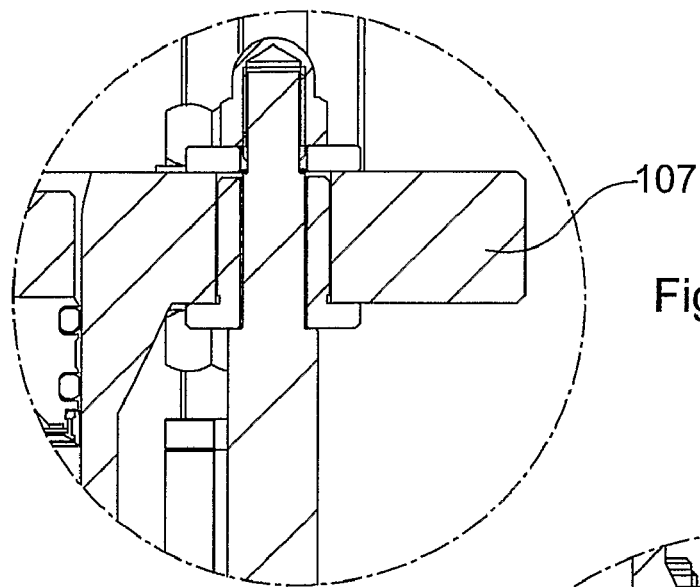
Figure 16:
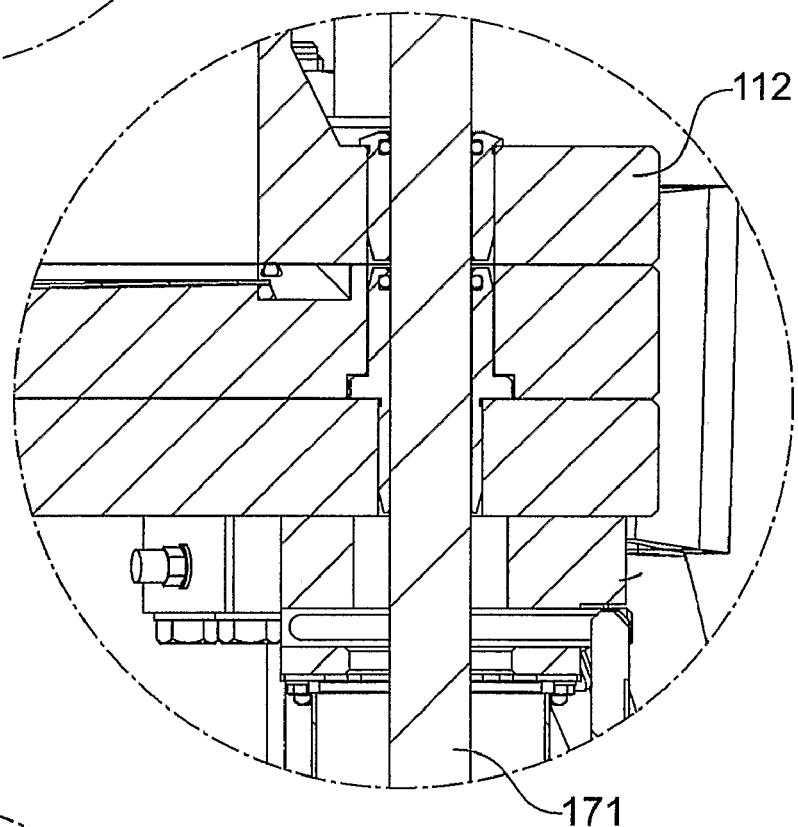
Figure 17:
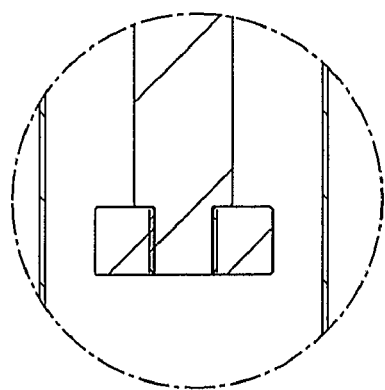
Figure 18:
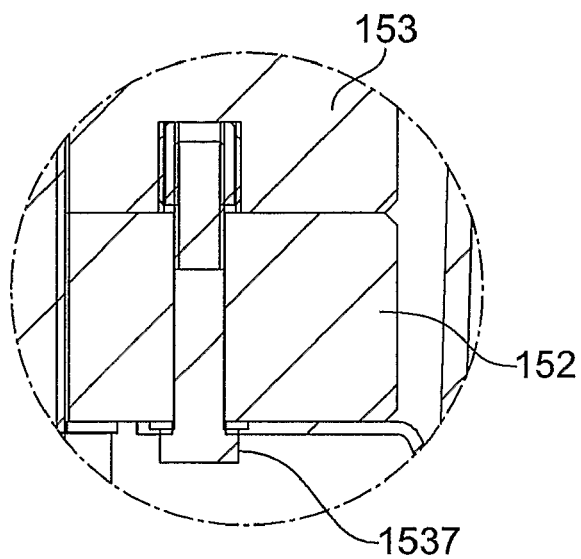
Figure 19:
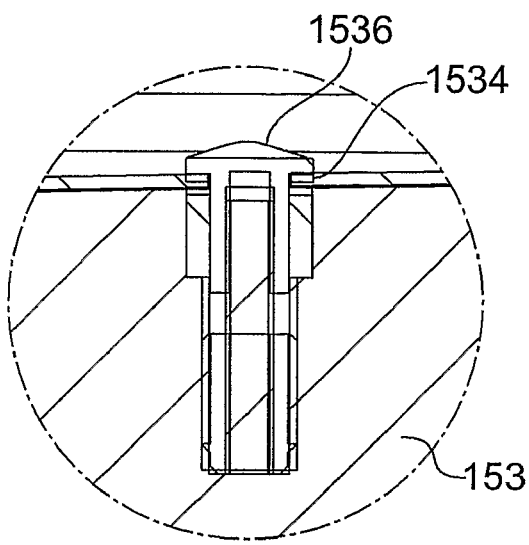
Figure 20:
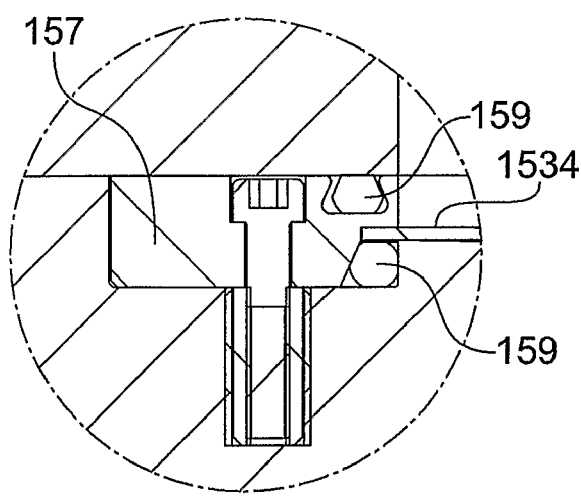

Examples of aspects of the invention are now discussed with reference to the remainder of the following drawings in which:

FIG. 6 is an axial section through a chromatography column, at VI of FIG. 8;

FIG. 7 is an axial cross-section of the same column at VII of FIG. 8;

FIG. 8 is a top view of the column;

FIG. 9 is an enlarged underneath view (in which, as in FIG. 7, the stand has been omitted for clarity);

FIGS. 10, 11 and 12 are first, second and third stages of an end cell access or maintenance procedure involving mesh removal, analogous to FIGS. 1 to 5 above;

FIG. 13 has enlarged detail at XIII of FIG. 7, where a drive rod meets the upper tube flange;

FIG. 14 shows detail at XIV of FIG. 7, where the drive rod passes through the base plate;

FIG. 15 is enlarged detail at XV of FIG. 7, where a guide rod secures into the tube flange;

FIG. 16 is enlarged detail at XVI of FIG. 7, where the guide rod passes through the base plate, also showing a safety mechanism;

FIG. 17 shows enlarged the bottom of the guide rod, at XVII in FIG. 7;

FIG. 18 is detail at XVIII of FIG. 6, showing securement of the fixed cell plate to the fixed cell backing plate;

FIG. 19 shows enlarged detail of a retaining screw for an end mesh;

FIG. 20 shows enlarged a bed support seal structure, seen also in FIG. 14, and

Figure 21:
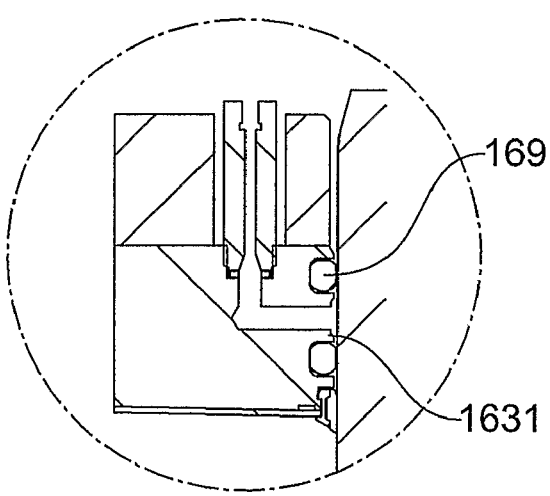

FIG. 21 shows enlarged an arrangement for flushing out the seals of the piston cell.

DETAILED DESCRIPTION OF PREFERRED EMBODIMENTS

The column components are broadly similar to those in FIGS. 1 to 5 discussed previously. Thus, the cylindrical stainless steel column tube 101 has upper and lower integral flanges 111, 112, and the base 105 consists of a steel backing plate 152 and a contoured cell plate 153 which carries the bed support mesh. Releasable threaded studs 157 hold the bottom column flange 112 down onto the base, clamping a fixed seal 159 described later. The column base 105 stands on support legs 151, here a wheeled mobile support, providing a component space beneath the base.

Continuing with reference to FIGS. 6 to 9, three hydraulic drive cylinders 108 are mounted to the underside of the base plate 152, and each operates a drive rod 181 extending up slidably through an opening in the base 105, a corresponding opening in the lower tube flange 112 and up to the upper flange 111. The upper flange 111 has corresponding holes, and a drive extension rod 183 has its bottom end passing through this flange opening and threadedly secured to the top of the main drive rod 181. At the upper flange 111, a pair of releasable nuts 184 can be used to lock the drive rod extension 183 to the flange 111, or released so that the rod can slide through it.

The top of each of the three drive rod extensions 183 is bolted into the outer periphery of a lifting ring 107. From its inner periphery, a circumferential series of nine spacer rods 166 depends vertically, their bottom ends being screwed fixedly into the back plate 162 of the upper cell piston 106. The spacer rods 166 are slightly longer than the interior axial length of the column tube 101.

Guide rods 171 are provided to guide and limit the movement between the column tube 101 and the base 105 when these are disconnected. The top end of each guide rod 171 is fixed into the top column flange 111, unlike the previously-described system in which they had to extend up to the lifting ring 7. The bottom of each guide rod passes down through slide openings in the bottom tube flange 111 and base 5 into a housing sleeve 178 extending down beneath the base 105. The bottom of each guide rod 171 has a projecting stop portion 177 (see also FIG. 17) which, by abutting beneath the plate 105, limits the height to which the tube 101 can be lifted above the base.

FIGS. 7 and 16 also show a safety plate 176 which, when the guide rod 171 is fully raised, can be slid across to block its return path and thereby support the raised assembly through the guide rods 171.

FIGS. 10, 11 and 12 show the stages involved in gaining access to the end cells of the column. Firstly (FIG. 10) the piston 106 is lowered by the drives 108 to its lowest available operating position in the tube 101. For this, the drive rod extensions 183 must be free to slide through the top tube flange 111. The fastener studs 157 are removed to release the tube 101 from the base 5.

The nuts 184 are then secured to lock the column tube 101 to the drive via its upper flange 111, and the drive rods 181, 183 extended to their full height. This height is limited by the abutment of the guide rod stops 177 against the underside of the base plate. The safety slides 176 are then pushed across, relieving the drive mechanism of the load. In this position, as in previous techniques, the bottom end cell is available for access.

To access the upper end cell, however, it is not necessary to re-lower the tube 101. Rather, the retaining nuts 184 securing the tube flange 111 to the drive rods 183 are released. The tube is then supported solely by the guide rods 171. The drive is then partially retracted to the position shown in FIG. 12, in which the entire front plate and end mesh of the piston end cell 6 emerge from the bottom end of the column tube 101. This is possible because the length of the spacing pillars 166, and the vertical reach of the drive rod extensions 183 in the other direction, is greater than the length of the tube. The end cell construction is then readily accessible for operations of the kind described, and its mesh can be removed or installed through the same clearance as is used for the bottom cell mesh.

Having thus described the essential advantageous operation of the column, some particular features are now described in a little more detail and with reference to FIGS. 13 to 21.

FIGS. 13, 14 show details of where the hydraulic drive passes through the upper and lower tube flanges 111,112 and base plates 152,153, and the connection of the first drive rod 181 to the drive rod extension 183. FIG. 13 also shows that, at the top opening of the column, the corner between the column bore and the flange top has a chamfer 114 to facilitate insertion of the sealed piston structure. The seals are elastomeric rings 169 seated in outwardly-directed peripheral grooves of the top cell plate 163, which in this embodiment is machined from engineering plastics. The plate edge is formed with an intermediate land 1631 between the two sealing rings 169, and a front land 1632 which retains the front sealing ring 169 and also mounts the retaining ring 1633 of the removable mesh layer 1634. FIG. 14 shows that the bottom edge of the tube bore has no chamfer, because exact cylindricality is crucial in this area. When the piston seals 169 are pushed out beyond the tube end for maintenance, the built-up lands 1631, 1632 support them against possibly damaging deformation, particularly as the piston is retracted after maintenance.

The seal arrangement at the bottom of the column does not slide. Instead, a mesh clamping ring 157 seats in an annular recess of the base plate 153 (see also FIG. 20), and has an inward shoulder which traps the edge of the lower mesh 1534 down against a ring seal 159. An opposed upward ring seal 159 engages the bottom face of the column tube.

FIG. 19 shows one of an array of fastening screws used to hold the mesh 1534 in place against the underlying end cell plate 153. This plate is machined with a pattern of surface grooves (not shown) for fluid flow behind the mesh. The fastening screws 1536 connect through into lands between these channels. The maintenance access spacing is sufficient to release or re-fasten these screws.

FIG. 18 shows a separate set of screws 1537 which keep the base plate 152 and bottom end cell plate 153 fixed together even when the studs 157 are released to release the column tube.

FIG. 21 shows an arrangement for flushing out the top cell seal construction, by forcing in pressurised liquid through a duct leading to openings in the land 1631 between the two sealing rings 169.

Finally, the hydraulic supplies to the three drives 108 are controllable independently of one another. Electronic monitors (not shown) read the axial positions of the drives and compare them, by means of a control processor. The control processor (not shown) is operatively connected to the hydraulic control and adjusts the hydraulic supplies to the respective drives 108 in dependence on the monitored values, equalising the axial extensions of the three drive rods 181. The skilled person will appreciate that this system is also used when the column is closed and preparing for operation, e.g. in adjusting the compression of the bed of chromatography medium. Any suitable hydraulic fluid may be used. Gas may be used instead.

The invention claimed is:

1. A method of operating chromatography column apparatus; the apparatus comprising a column tube having first and second ends, and first and second discrete end cell structures which are associated with the respective ends of the column tube and positionable to close off the column tube and thereby define therein a column space for retaining chromatography medium, in use of the apparatus; at least the first end cell structure comprising a piston portion fitting slidably in the column tube;

the operating method comprising separating the second end of the column tube and the second end cell structure to provide an access spacing between them moving a safety plate and blocking movement of the second end of the column tube toward the second end cell structure to maintain the access spacing, advancing the piston portion of the first end cell structure through the column tube to expose it at the open second end of the column tube, and carrying out maintenance of the piston portion thus exposed.

2. The method according to claim 1 in which the column tube is axially vertical with said first and second ends at the top and bottom respectively.

3. The method according to claim 1, comprising using a powered drive, mounted on or adjacent the second end structure, to separate the column tube and the second end cell structure to provide said access spacing.

4. The method according to claim 3, comprising operating the powered drive to separate the column tube and second end cell structure, and to move the piston portion through the column tube.

5. The method according to claim 3, comprising hydraulically actuating the powered drive.

6. The method according to claim 1, comprising using a powered drive to move said piston portion relatively forwardly through the column tube to be exposed at the second end thereof as aforesaid.

7. The method according to claim 1, wherein the piston portion is supported from behind by an insertable support structure that reaches in from the first end of the column tube, with sufficient axial reach for the front of the piston portion to reach beyond the second end of the column tube for said maintenance.

8. The method according to claim 7, comprising operating a powered drive and advancing the piston portion to said exposed position by means of a drive connection via said insertable support structure.

9. The method according to claim 8 wherein the powered drive comprises plural hydraulically-actuated drive rods extending axially up the outside of the column tube, said drive rods being circumferentially spaced from one another, driven by cylinders mounted at or adjacent the second end cell structure, and connected to the insertable support structure by a radial connecting structure which crosses radially above the edge of the column tube at the first end thereof.

10. The method according to claim 9 wherein said drive rods are driven by cylinders mounted below the second end cell structure.

11. The method according to claim 7, wherein the insertable support structure has sufficient axial reach for the front of the piston portion to project beyond the second end of the column tube for said maintenance.

12. The method according to claim 1, wherein separating the second end of the column tube and the second end cell structure to provide an access spacing between them includes moving guide rods having projecting stops limiting the height to which the second end of the column tube can be separated from the second end cell structure.

* * * * *